United States Patent
Johnson, II et al.

(10) Patent No.: US 11,624,755 B2
(45) Date of Patent: Apr. 11, 2023

(54) GAIT-PACE METER AND METHODS OF DETERMINING GAIT SPEED

(71) Applicants: Georgia Tech Research Corporation, Atlanta, GA (US); Emory University, Atlanta, GA (US)

(72) Inventors: Theodore Michael Johnson, II, Atlanta, GA (US); Leigh Nadel, Atlanta, GA (US); Ann Vandenberg, Atlanta, GA (US); Brian Jones, Atlanta, GA (US); Priyanka Sadananda, Atlanta, GA (US); Mei Ling Sharon Ang, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 363 days.

(21) Appl. No.: 16/971,764

(22) PCT Filed: Feb. 21, 2019

(86) PCT No.: PCT/US2019/018933
§ 371 (c)(1),
(2) Date: Aug. 21, 2020

(87) PCT Pub. No.: WO2019/165056
PCT Pub. Date: Aug. 29, 2019

(65) Prior Publication Data
US 2021/0048446 A1 Feb. 18, 2021

Related U.S. Application Data

(60) Provisional application No. 62/633,148, filed on Feb. 21, 2018.

(51) Int. Cl.
*G01P 3/68* (2006.01)
*G01C 23/00* (2006.01)
*G06F 3/16* (2006.01)

(52) U.S. Cl.
CPC ............ *G01P 3/68* (2013.01); *G01C 23/00* (2013.01); *G06F 3/165* (2013.01)

(58) Field of Classification Search
CPC ............ G01P 3/68; G06F 3/165; G01C 23/00
(Continued)

(56) References Cited

U.S. PATENT DOCUMENTS 5,831,937 A * 11/1998 Weir .................. A61B 5/1038
367/128
7,535,368 B2 5/2009 Graichen et al.
(Continued)

OTHER PUBLICATIONS

Search Report from Application No. PCT/US2019/018933 dated Jun. 22, 2020 (9 pages).
(Continued)

*Primary Examiner* — Nathaniel T Woodward
(74) *Attorney, Agent, or Firm* — Troutman Pepper Hamilton Sanders LLP; Ryan A. Schneider; Korbin M. Blunck (57) ABSTRACT

Embodiments of the present disclosure relate generally to systems and methods of measuring speed and, more particularly, to systems and methods of measuring gait speed using a plurality of sensors. The systems described herein may include sensing units comprising one or more motion sensors for detecting a patient walking along a testing distance. In some embodiments, a controller may calculate a gait speed based at least in part on the testing distance and on signals received from the sensors. In some embodiments, an initiation input may be provided to activate the systems. In some embodiments, the initiation input may also provide a target to which a patient can walk.

20 Claims, 4 Drawing Sheets

(58) Field of Classification Search
USPC .......................................................... 73/54.03
See application file for complete search history.

(56) References Cited

U.S. PATENT DOCUMENTS

| | | | |
|---|---|---|---|
| 9,642,415 B2* | 5/2017 | Pease | A43B 3/0031 |
| 2006/0036396 A1 | 2/2006 | Brown | |
| 2008/0269644 A1* | 10/2008 | Ray | A61B 5/224 |
| | | | 600/587 |
| 2011/0153545 A1* | 6/2011 | Greene | A61B 5/1113 |
| | | | 706/54 |
| 2011/0190667 A1* | 8/2011 | Alwan | G06K 9/00496 |
| | | | 600/595 |
| 2012/0253234 A1 | 10/2012 | Yang et al. | |
| 2016/0120733 A1 | 5/2016 | Ishikawa et al. | |

OTHER PUBLICATIONS

Ousing, et al., "A Normative Sample of Temporal and Spatial Gait Parameters in Children Using the GAITRite Electronic Walkway," Gait & Posture 25.1, 2007 pp. 135-139.

* cited by examiner

GAIT-PACE METER AND METHODS OF DETERMINING GAIT SPEED

CROSS-REFERENCE TO RELATED APPLICATIONS

This Application claims priority to U.S. Provisional Patent Application No. 62/633,148, filed 21 Feb. 2018, which is hereby incorporated by reference herein in its entirety as if fully set forth below.

STATEMENT OF RIGHTS UNDER FEDERALLY SPONSORED RESEARCH

This invention was made with government support under Grant No. RE5016 awarded by the U.S. Department of Health and Human Services, and under Grant No. TR000454 awarded by the National Institutes of Health. The government has certain rights in the invention.

FIELD OF THE DISCLOSURE

Embodiments of the present disclosure relate generally to systems and methods of measuring speed and, more particularly, to systems and methods of measuring gait speed using a plurality of sensors.

BACKGROUND

The population of adults over the age of 65 is steadily growing and is only expected to continue growing over the next few decades. As a result of the population growth in this age group, researchers and clinicians have placed a great deal of focus on determining the factors that lead to health outcomes such as survival, hospitalization, and injury. Studies support that gait speed, combined with gender and age, can serve as a valid predictor for these outcomes. Gait speed of a patient, for example, has been shown to be a reliable indicator of the patient's life expectancy.

However, despite its potential to inform the appropriateness of health-related decisions, gait speed measurement is not routinely incorporated into primary-care settings. Lack of widespread adoption and use of gait speed measurement in clinical settings likely stems from the complexity of integrating the assessment into a clinic's workflow. Current systems for measuring gait speed produce hurdles to implementation, hurdles including cost, ease of use, and reliability.

The most common method of determining gait speed is using a stopwatch. Stopwatch measurement requires first measuring and marking a distance to be traveled. Then, the staff administering the test must provide verbal instructions for the patient to begin. Stopwatch measurement can be unreliable because accuracy depends on verbal instructions and testing distance. If the staff member stands at the end of the testing distance, it may be difficult for the staff member to determine when to start the time; if the staff member stands at the beginning of the testing distance, it may be difficult to determine when to stop the time. Therefore, although stopwatch measurement is cost effective, the method is lacking in ease of use and reliability.

Another method of determining gait speed is using pressure mapping mats. These mats measure gait speed by tracking footfall. Pressure mapping maps are accurate, as the time and distance are processed digitally by assessing footfall. The method does, however, provide its own hurdles. The mats are very expensive, as high as $100,000, and they typically remain on the floor when not in use. A mat on the floor poses a potential tripping hazard, particularly for clinics seeing geriatric patients. The accuracy gained with these mats, therefore, comes with a decrease in ease of use and a decrease in cost effectiveness.

Another method of determining gait speed is using an RFID wearable with a corresponding RFID reader. These systems can also be accurate. The accuracy, however, depends on the range of the RFID system—if the patient walks beyond of the range of the RFID system, the test failed. The main pitfall for RFID systems is the wearable device required to determine gait speed. A wearable must be stored, maintained, and most importantly, not lost. The RFID wearable provides the greatest hurdle for the system, ease of use.

Other methods are known, but all suffer from either being inaccurate, expensive, unreliable, or some combination thereof. Because gait speed is a valuable predictor of health, what is needed is a system that provides a reliable, accurate, and cost-effective solution for clinics so that gait-speed analysis can be incorporated into the primary-care setting. The system should also be easy to operate to ensure gait speed analysis is easily performed within the clinic's workflow.

SUMMARY

Embodiments of the present disclosure address these concerns as well as other needs that will become apparent upon reading the description below in conjunction with the drawings. Briefly described, embodiments of the present disclosure relate generally to systems and methods of measuring speed and, more particularly, to systems and methods of measuring gait speed using a plurality of sensors.

An exemplary embodiment of the present invention provides a gait speed monitoring system comprising a first motion sensing unit comprising a first sensor, and a second motion sensing unit comprising a second sensor. The first sensing unit can be spaced apart from the second sensing unit by a testing distance. The system can further comprise a controller. The controller is configured to receive a first signal from the first sensor when the first sensor detects motion. The controller is configured to receive a second signal from the second sensor when the second sensor detects motion. The controller is configured to calculate a gait speed, wherein the gait speed is based at least in part on the first signal, the second signal, and the testing distance.

In any of the embodiments described herein, the system can comprise a first initiation input, wherein the controller is configured to, upon an input to the first initiation input, cause the first sensing unit to begin detecting motion.

In any of the embodiments described herein, the system can comprise a second initiation input, wherein the controller is configured to, upon an input to the second initiation input, cause the second sensing unit to begin detecting motion.

In any of the embodiments described herein, the first initiation input can be spaced apart from the second initiation input by a distance greater than the testing distance.

In any of the embodiments described herein, the first initiation input can be spaced apart from the first sensing unit by a distance of at least 3 feet.

In any of the embodiments described herein, the second initiation input can be spaced apart from the second sensing unit by a distance of at least 3 feet.

In any of the embodiments described herein, the second initiation input can be configured to illuminate as a walking target.

In any of the embodiments described herein, the first initiation input can be configured to illuminate as a walking target.

In any of the embodiments described herein, the second initiation input can be configured to provide an audible signal as a walking target.

In any of the embodiments described herein, the first initiation input can be configured to provide an audible signal as a walking target.

In any of the embodiments described herein, the controller can be configured to, upon an input to the first initiation input, cause the second initiation input to illuminate as a walking target.

In any of the embodiments described herein, the controller can be configured to, upon an input to the second initiation input, cause the first initiation input to illuminate as a walking target.

In any of the embodiments described herein, the first sensing unit and the second sensing unit can be positioned horizontal and in a walkway.

In any of the embodiments described herein, the first sensing unit and the second sensing unit can be positioned from between 3 feet and 5 feet above a ground level of a walkway.

In any of the embodiments described herein, the first sensing unit and the second sensing unit can be positioned upon a wall along a walkway.

In any of the embodiments described herein, the first sensing unit and the second sensing unit can be positioned on a ceiling.

In any of the embodiments described herein, the first sensing unit can be configured to provide at least one of a visual or audible feedback when the first sensor detects motion, and the second sensing unit can be configured to provide at least one of a visual or audible feedback when the second sensor detects motion.

In any of the embodiments described herein, the first sensing unit can comprise a third sensor that detects motion. The second sensing unit can comprise a fourth sensor that detects motion. The controller can be configured to receive a third signal from the third sensor when the third sensor detects motion, and receive a fourth signal from the fourth sensor when the fourth sensor detects motion. The gait speed can be based at least in part on the third signal, the fourth signal, and the testing distance.

In any of the embodiments described herein, the first sensor can be one of a passive infrared motion detector, a proximity sensor, or an ultrasonic rangefinder.

In any of the embodiments described herein, the second sensor can be one of a passive infrared motion detector, a proximity sensor, or an ultrasonic rangefinder.

In any of the embodiments described herein, the first sensor can be a passive infrared motion detector; the second sensor can be a passive infrared motion detector; the third sensor can be one of a proximity sensor or an ultrasonic rangefinder; and the fourth sensor can be one of a proximity sensor or an ultrasonic rangefinder.

In any of the embodiments described herein, the first sensing unit can be configured to provide at least one of a visual or audible feedback when the first sensor or the third sensor detects motion. The second sensing unit can be configured to provide at least one of a visual or audible feedback when the second sensor or the fourth sensor detects motion.

In any of the embodiments described herein, the controller can be a mobile device.

In any of the embodiments described herein, the system can further comprise a display unit configured to display the gait speed.

In any of the embodiments described herein, a display unit can be a mobile device.

In any of the embodiments described herein, the controller can be configured to transmit the gait speed to a database.

In any of the embodiments described herein, the controller can be configured to, upon an input to the first initiation input, cause the first sensing unit to begin detecting motion. The controller can be configured to, upon receiving a signal from the first sensing unit indicating that the first sensor detected motion, cause the second sensing unit to begin detecting motion.

In any of the embodiments described herein, the controller can be configured to, upon an input to the second initiation input, cause the second sensing unit to begin detecting motion. The controller can be configured to, upon receiving a signal from the second sensing unit indicating that the second sensor detected motion, cause the first sensing unit to begin detecting motion.

In any of the embodiments described herein, the controller can be configured to compare the calculated gait speed to a predetermined range of acceptable gait speeds. The controller can be configured to censor the calculated gait speed if the calculated gait speed is outside of the predetermined range of acceptable gait speeds.

Another exemplary embodiment provides a method of determining gait speed. The method can include providing a gait speed monitoring system. The gait speed monitoring system can comprise a first motion sensing unit comprising a first sensor, and a second motion sensing unit comprising a second sensor. The first sensing unit can be spaced apart from the second sensing unit by a testing distance. The system can further comprise a controller. The controller is configured to receive a first signal from the first sensor when the first sensor detects motion. The controller is configured to receive a second signal from the second sensor when the second sensor detects motion. The controller is configured to calculate a gait speed, wherein the gait speed is based at least in part on the first signal, the second signal, and the testing distance. The method can further comprise directing a patient to walk across the testing distance. The method can further comprise receiving a calculated gait speed from the controller.

In any of the embodiments described herein, the gait speed monitoring system can further comprise a first initiation input, wherein the controller is configured to, upon an input to the first initiation input, cause the first sensing unit to begin detecting motion. The method can further comprise providing an input to the first initiation input.

In any of the embodiments described herein, the gait speed monitoring system can further comprise a second initiation input, wherein the controller is configured to, upon an input to the second initiation input, cause the second sensing unit to begin detecting motion. The method can further comprise providing an input to the second initiation input. The method can further comprise directing the patient to walk from the second initiation input, across the testing distance, and to the first initiation input.

In any of the embodiments described herein, the first initiation input can be spaced apart from the second initiation input by a distance greater than the testing distance.

In any of the embodiments described herein, the first initiation input can be spaced apart from the first sensing unit by a distance of at least 3 feet.

In any of the embodiments described herein, the second initiation input can be spaced apart from the second sensing unit by a distance of at least 3 feet.

In any of the embodiments described herein, the second initiation input can be configured to illuminate as a walking target.

In any of the embodiments described herein, the first initiation input can be configured to illuminate as a walking target.

In any of the embodiments described herein, the second initiation input can be configured to provide an audible signal as a walking target.

In any of the embodiments described herein, the first initiation input can be configured to provide an audible signal as a walking target.

In any of the embodiments described herein, the controller can be configured to, upon an input to the first initiation input, cause the second initiation input to illuminate as a walking target.

In any of the embodiments described herein, the controller can be configured to, upon an input to the second initiation input, cause the first initiation input to illuminate as a walking target.

In any of the embodiments described herein, the first sensing unit and the second sensing unit can be positioned horizontal and in a walkway.

In any of the embodiments described herein, the first sensing unit and the second sensing unit can be positioned from between 3 feet and 5 feet above a ground level of a walkway.

In any of the embodiments described herein, the first sensing unit and the second sensing unit can be positioned upon a wall along a walkway.

In any of the embodiments described herein, the first sensing unit and the second sensing unit can be positioned on a ceiling.

In any of the embodiments described herein, the first sensing unit can be configured to provide at least one of a visual or audible feedback when the first sensor detects motion, and wherein the second sensing unit is configured to provide at least one of a visual or audible feedback when the second sensor detects motion.

In any of the embodiments described herein, the first sensing unit can comprise a third sensor that detects motion. The second sensing unit can comprise a fourth sensor that detects motion. The controller can be configured to receive a third signal from the third sensor when the third sensor detects motion, and receive a fourth signal from the fourth sensor when the fourth sensor detects motion. The gait speed can be based at least in part on the third signal, the fourth signal, and the testing distance.

In any of the embodiments described herein, the first sensor can be one of a passive infrared motion detector, a proximity sensor, or an ultrasonic rangefinder.

In any of the embodiments described herein, the second sensor can be one of a passive infrared motion detector, a proximity sensor, or an ultrasonic rangefinder.

In any of the embodiments described herein, the first sensor can be a passive infrared motion detector; the second sensor can be a passive infrared motion detector; the third sensor can be one of a proximity sensor or an ultrasonic rangefinder; and the fourth sensor can be one of a proximity sensor or an ultrasonic rangefinder.

In any of the embodiments described herein, the first sensing unit can be configured to provide at least one of a visual or audible feedback when the first sensor or the third sensor detects motion. The second sensing unit can be configured to provide at least one of a visual or audible feedback when the second sensor or the fourth sensor detects motion.

In any of the embodiments described herein, the controller can be a mobile device.

In any of the embodiments described herein, the gait speed monitoring system can further comprise a display unit configured to display the calculated gait speed.

In any of the embodiments described herein, the display unit can be a mobile device.

In any of the embodiments described herein, the controller can be configured to transmit the calculated gait speed to a database.

In any of the embodiments described herein, the controller can be configured to, upon an input to the first initiation input, cause the first sensing unit to begin detecting motion. The controller can be configured to, upon receiving a signal from the first sensing unit indicating that the first sensor detected motion, cause the second sensing unit to begin detecting motion.

In any of the embodiments described herein, the controller can be configured to, upon an input to the second initiation input, cause the second sensing unit to begin detecting motion. The controller can be configured to, upon receiving a signal from the second sensing unit indicating that the second sensor detected motion, cause the first sensing unit to begin detecting motion.

In any of the embodiments described herein, the method can further comprise walking with the patient across the testing distance.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE FIGURES

Reference will now be made to the accompanying figures and diagrams, which are not necessarily drawn to scale, and wherein.

DETAILED DESCRIPTION

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. In particular, the presently disclosed subject matter is described in the context of being a system and method for determining gait speed. The present disclosure, however, is not so limited and can be applicable in other contexts. For example, and not limitation, some embodiments of the present disclosure may improve the functionality of speed sensing technologies in other contexts, such as measuring the speed of non-animal objects. Additionally, some embodiments of the present disclosure may improve upon motion-sensing technologies other than technologies for determining speed. These embodiments are contemplated within the scope of the present disclosure. Accordingly, when the present disclosure is described in the context of systems for and methods of determining gait speed, it will be understood that other embodiments can take the place of those referred to.

Throughout this disclosure, the terms patient and subject are used interchangeably, and both means a person being testing by the gait measurement system or method. Also, the terms physician, caregiver, provider, and therapist are used throughout this disclosure. These terms refer to a person administering a gait measurement and are used interchangeably. The methods described herein are not limited to being performed by certain persons or professions, however. It is conceived that the systems and methods described herein can be performed by any person, including the person whose gait is being measured, i.e., self-testing. This is because of the ease of use associated with the present systems and methods. Therefore, when the disclosure refers to the person administering or initiating a gait measurement test, it will be understood that the description and/or profession of the person is merely descriptive and exemplary, not limiting.

As described above, several current methods of determining a person's gait speed exist in the market. One method is using a stopwatch and testing over a marked distance. The reliability and accuracy of this method depends heavily on the adequacy of the instructions given to the patient. Also, the staff member giving the instructions must know when to start and stop the time, based only on the staff member's perception of when the patient or subject crosses the start and finish line. Another aspect of stopwatch measurement that leads to error is the acceleration and deceleration period of a patient. If a patient or subject stands at the starting line of the testing distance, then the gait speed measurement may be skewed because of a certain amount of acceleration time needed for the person to reach a normal gait speed. Also, if a patient or subject does not continue walking beyond the finish line of the testing distance, then the measurement may be skewed due to the person's deceleration before the test is complete. These additions of human error can cause gait measurement by stopwatch to be less than reliable for widespread clinical use.

Other methods, such as using pressure sensing mats or RFID systems, for determining gait speed are used sparingly in research settings, and even more sparingly in clinical settings. These methods suffer from high costs and/or being difficult to implement in the workflow of a clinic or hospital. These difficulties stem from storing and maintaining the equipment. A pressure mat, for example, must be removed from the walkway once the test is complete. Alternatively, the pressure mat can remain on the floor, but this creates a potential tripping hazard should the mat be in a walkway, or this creates the need for additional clinical space that is dedicated for gait measurement. Often, the pressure mat also requires a dedicated operator to run the system and process the results. One additional hurdle for implementing the pressure mat is the system's cost, which can be as high as $100,000. An RFID system may provide a more affordable alternative to the pressure mat, but the system includes the extra hassle of maintaining the RFID wearable required for the measurement. The RFID wearable adds another step into the clinic's workflow, requiring the patient to receive the RFID wearable from a staff member and requiring the patient to place the tag somewhere on his or her body before the test can be performed.

The hurdles to widespread adoption of gait speed analysis in the clinical setting causes an unfortunate absence of the test in the continuum of care. Assessing a patient's gait speed at regular clinical visits would provide countless benefits for patient care. Studies show that gait speed is a predictor of mortality. The assessments could also provide a point of conversation between a patient and a physician: if a patient's gait speed is decreasing, the doctor may wish to discuss that with the patient. For therapists, providing an additional, objective measure can help the therapist tailor individualized care for the patient. Finally, if gait speed is tracked regularly, it is possible for a provider to know exactly how a patient is progressing in their care.

The present disclosure describes cost effective, accurate systems and methods for determining gait speed. In some embodiments, the systems and methods described herein comprise motion sensors for detecting motion. In some embodiments, the systems and methods provide features to produce a more accurate measurement by (1) reducing human error in communicating the steps of the measurement to a patient and (2) providing real-time feedback on measurement success. Various systems and methods are disclosed for measuring gait speed, and exemplary embodiments of the systems and methods will now be described with reference to the accompanying figures.

Figure 1:
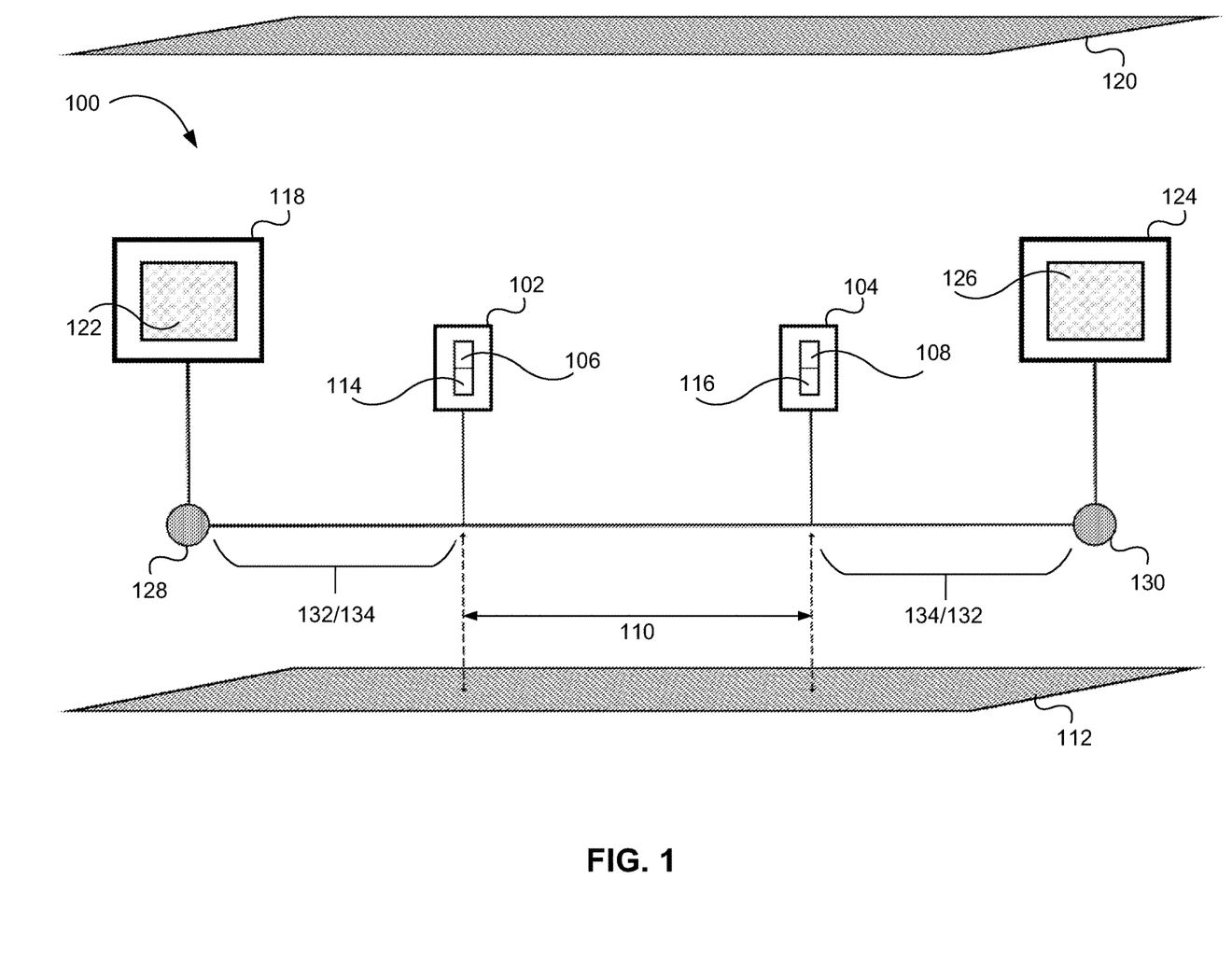
FIG. 1 depicts an exemplary gait-pace meter, according to some embodiments of the present disclosure.

FIG. 1 depicts an exemplary gait-pace meter 100, according to some embodiments. In some embodiments, a gait-pace meter 100 may have a first motion sensing unit 102 and a second motion sensing unit 104. The motion sensing units 102,104 comprise sensors for detecting when a person passes by the motion sensing units 102,104. For example, the first sensing unit 102 may comprise a first sensor 106, and the second sensing unit 104 may comprise a second sensor 108. In some embodiments, the motion sensing units 102,104 may be separated from each other by a testing distance 110. The gait speed can be determined by the time between the first sensor 106 detecting motion and the second sensor 108 detecting motion, divided by the testing distance 110. In some embodiments, the systems are bidirectional, meaning that the gait speed can also be determined by the time between the second sensor 108 detecting motion and the first sensor 106 detecting motion, divided by the testing distance 110. The testing distance 110 can be any distance desired for a gait analysis. For example, if the gait-pace meter 100 is being used in a clinical setting, the testing distance 110 may be determined based on the length of an available walkway 112, such as a portion of a hallway. It is contemplated that a testing distance 110 may be from a few feet to several meters long. For example, certain embodiments of the present systems and methods were tested over a testing distance 110 of four meters, which is in accordance with some embodiments.

In some embodiments, the gait-pace meter 100 comprises more than a two sensing units, each with one or more sensors. In some embodiments, the gait-pace meter 100 may assess a patient's gait speed over a plurality of segments. For example, some embodiments may have a first sensor 106 in a first sensing unit 102, a second sensor 108 in a second sensing unit 104, and an additional sensor in a third sensing unit (not shown in FIG. 1). In this embodiment, the systems may calculate a time between the first sensor 106 detecting motion and the second sensor 108 detecting motion and divide by the distance of that segment; then the systems may calculate a time between the second sensor 108 detecting motion and the additional sensor detecting motion, over the second segment distance; the systems may calculate the gait speed across these two segments and, in some embodiments, average the two speeds. Again, any embodiment described herein may be bidirectional, meaning the segments could be in reverse. Any number of sensing units is possible with the present systems and methods.

In some embodiments, a sensing unit 102,104 may comprise a plurality of sensors. For example and not limitation, the first sensing unit 102 may comprise third sensor 114 (i.e., the first sensing unit 102 comprises two sensors—the first sensor 106 and the third sensor 114), and the second sensing unit 104 may comprise a fourth sensor 116 (i.e., the second sensing unit 104 also comprises two sensors—the second sensor 108 and the fourth sensor 116). Although not required in the present systems, multiple sensors 106,108,114,116 within each sensing unit 102,104 builds redundancy into the systems. For example, if a patient walks or moves across the testing distance 110 and passes the sensing unit 102,104, it may be possible that one sensor does not detect motion, but with additional sensors present within the sensing unit 102,104, it is less likely that both sensors fail to detect the patient's passing. In some embodiments, a sensing unit 102,104 may comprise more than two sensors. It is to be understood that, when reference is made to a signal coming from a sensing unit 102,104, this refers to a signal being transmitted from one of the sensors 106,108,114,116 within the individual sensing unit 102,104. Also, when reference is made to a sensing unit 102,104 detecting motion, this refers to one of the sensors within the individual sensing unit 102,104 detecting motion.

In some embodiments, the sensors 106,108,114,116 described herein may be any sensor known in the art that may be used for detecting motion or presence of an object. For example and not limitation, the sensors 106,108,114,116 may be passive infrared motion detectors, proximity sensors, ultrasonic rangefinders, and/or any other motion or presence sensor known in the art. Detecting motion can include detecting actual motion of the patient or detecting presence of a patient in a sensor's field. A proximity sensor and an ultrasonic rangefinder, for example, may be used in a system to detect presence of a patient within the sensor's field; thus in some embodiments, sensors may be adjusted to customize a width of the sensing zone. In some embodiments, multiple types of sensors may be present within a single sensing unit 102,104. Although not required in the present systems, a single sensing unit 102,104 with multiple types of sensors builds redundancy into the systems. An example, but not limitation, of this redundancy is when a single sensing unit 102,104 comprises a passive infrared motion detector and a proximity sensor. The passive infrared motion detector may have a greater range and lower sensitivity, and the proximity sensor may have a greater sensitivity and lower range. Such an embodiment can help improve the accuracy of the gait-pace meter 100. The same redundancy could be included by providing an ultrasonic rangefinder.

In some embodiments, a sensing unit 102,104 may be positioned within a hallway. In some embodiments, a sensing unit 102,104 may be positioned upon a wall along a walkway 112, e.g., a wall of the hallway. Positioned upon a wall is to be understood to mean upon the surface of a wall between the floor of walkway 112 and a ceiling of the walkway 120. A sensing unit 102,104 may sit on top of the surface of the wall or may be set into the wall. In some embodiments, if a sensing unit 102,104 is set into the wall, the sensing unit 102,104 may be flush with the wall. In some embodiments, a sensing unit 102,104 may be disposed within a stand, wherein the stand is portable and may be repositioned in different areas of a clinic, hospital, or home. In any embodiment, a sensing unit 102,104 may be positioned horizontal to the surface of a walkway 112. Horizontal is to be understood to mean positioned such that the sensors 106,108,114,116 are pointed away from a wall and across a walkway 112 such that, as a patient walks along the walkway 112, the sensors 106,108,114,116 are able to detect motion of the patient walking. The sensors 106,108,114,116 are not required to be at 90° from the wall, however. The height of the sensing units 102,104 along the wall can be any height that may capture the gait of an individual. In some embodiments, the height of the sensing units 102,104 may be from between 3 feet and 5 feet from above the ground level of the walkway 112. This would allow most individuals to be captured by the sensors described herein. A height of 3 to 5 feet may also be above the average patient's legs, potentially providing improved results as the gait speed is not skewed by a patient's stride; in other words, if a patient is measured at their torso, the sensors may not be dependent upon stride placement. Other heights are also possible, and the height depends on the clinical setting, the types of patients (i.e., ambulatory vs. non-ambulatory), and the data to be gathered. In some embodiments, a sensing unit 102, 104 may be positioned on a ceiling 120. In this embodiment, the sensors 106,108,114,116 should be pointed towards the walkway 112 so that the sensors 106,108,114,116 may detect a person walking along the walkway 112.

In some embodiments, a sensing unit 102,104 may include visual or audible feedback to indicate when a sensor 106,108,114,116 detects motion. This may be beneficial during a test so that the person administering the test knows, instantaneously, whether the sensors 106,108,114,116 detected the patient walking. In some embodiments, the feedback may be in the form of a visual feedback including lighting housed within the sensing unit 102,104. An exemplary device may include lighting that illuminates if any one of the sensors 106,108,114,116 within a sensing unit 102, 104 detects motion. Using a first sensing unit 102 as an example (though any feedback method is possible for any sensing unit described herein), in some embodiments lighting within the first sensing unit 102 may illuminate if a first sensor 106 detects motion. The same lighting may also illuminate if a third sensor 114 detects motion. In some embodiments, a sensing unit 102,104 may have a set of lighting for each sensor so that the test administrator knows which sensor detected motion. Again using a first sensing unit 102 as an example, a first sensing unit 102 may comprise a first sensor 106 and a third sensor 114, each sensor 106,114 having its own lighting indicating which sensor detected motion. Some examples of this would be lights in certain positions of the first sensing unit 102 for the first sensor 106 and lights in a different position for the second sensor 114. Another example would be different colors lights for different sensors 106,114. Another example would be a display screen on the sensing units 102,104 that displays, with pictures, figures, or words, which sensor 106,108,114,116 detected motion. Each of these example visual feedback methods can be employed on any sensing unit 102,104 described herein.

In some embodiments, the feedback may be in the form of audible feedback. A sensing unit 102,104 may include a single sound, such that if any of the sensors 106,108,114,116 detect motion the sound is produced; in some embodiments, different types of sensors may have their own unique sounds. The sounds may be chimes, alarms, beeps, or any other sound that may inform the administrator of successful detection by one or more sensors. These feedback methods are exemplary and do not represent all types of visual or audible feedback possible with the current systems. Also, these feedback methods are not mutually exclusive, and any combination of these feedback methods are contemplated in a gait-pace meter 100 according to various embodiments of the present invention.

In some embodiments, a gait-pace meter 100 may comprise a controller 118. The controller may act to receive signals from any sensor 106,108,114,116 when the sensor detects motion. The controller 118 may receive a signal from a sensor 106,108,114,116 either over a wired connection or a wireless connection. In some embodiments, the controller 118 calculates the gait speed of the patient walking cross the testing distance 110. For example, in some embodiments, the controller 118 may receive a signal from the first sensor 106 when the first sensor 106 detects motion. The controller 118 may then calculate a time between receiving that first signal and receiving a signal from the second sensor 108 when the second sensor 108 detects motion. The controller can then calculate a gait speed by dividing the calculated time by a set testing distance 110. As described herein, the systems may be bidirectional, so the controller 118 may calculate gait speed based on a signal from the second sensing unit's 104 sensors then the first sensing unit's 102 sensors. Although a gait-pace meter 100 as described herein is not required to provide bidirectional analysis, in some clinical settings a bidirectional system may ease the incorporation of gait analysis into the clinic's workflow. In some embodiments, a single gait analysis can be performed from either end of the system. If a test is performed again for any reason, the test can be performed from the opposite end of a bidirectional system. In some embodiments, a controller 118 may save readings from multiple tests, and, in some embodiments, calculate an average based on the multiple tests.

In some embodiments, a controller 118 may calculate a gait speed based on signals from a third sensor 114 and a fourth sensor 116 in the same manner as described above for the first sensor 106 and second sensor 108. A controller 118 may not be able to calculate a gait speed if no sensor within a sensing unit 102,104 detects motion. This is an example of when redundancy in each sensing unit 102,104 may be beneficial. In embodiments with multiple sensors within a sensing unit 102,104, a controller 118 may calculate a gait speed if any sensor within the sensing unit 102,104 detects motion. In some embodiments, a controller 118 may only calculate a gait speed if like sensors detect motion. For example and not limitation, a controller 118 may calculate a gait speed only if a proximity sensor in a first sensing unit 102 and a proximity sensor in a second sensing unit 104 detects motions, but not if a passive infrared sensor in a first sensing unit 102 detects motion and a proximity sensor in the second sensing unit 104 detects motion. In some embodiments, a controller 118 may calculate a gait speed if any one of the sensors in any sensing unit 102,104 detects motion, regardless of the type of sensor.

In some embodiments, a controller 118 may be disposed on a wall within a walkway 112. A controller 118 may be located at or near the sensing units 102,104. In some embodiments, a controller 118 may be located at a particular distance from the sensing units 102,104. In some embodiments, the controller 118 may be positioned such that the controller is not placed between sensing units 102,104, but is instead positioned outside of the testing distance 110. In some embodiments, a controller 118 may be a separate computing device (described in greater detail in FIG. 2) that is located somewhere other than on the wall or on the ceiling 120 of the walkway 112. The separate computing device, for example, may be a computer, mobile device, or other device connected to a network, wherein the separate computing device may receive the signals from the sensing units 102,104 either over a wired or wireless connection.

In some embodiments, a controller 118 may include a display 122. A display 122 may be a light emitting diode display, a liquid crystal display, a plasma display, or any other display that may provide information to a test administrator or patient. The information provided by a display 122 may include a gait speed determined by the controller. In some embodiments, a display 122 may receive input from an administrator to set the testing distance 110; and a controller 118 may save the information so that all subsequent tests are preset with the testing distance 110. In some embodiments, the display may be separate from the controller 118. A display 122, for example, may be provided in a separate computing device, and the display 122 in the separate computing device may receive gait speed information sent from the controller over a wired or wireless connection. In some embodiments, a controller 118 may provide the visual or audible feedback of whether a sensor within a sensing unit 102,104 detected motion. For example and not limitation, the display 122 may indicate which sensors detected motion, and the sounds indicating which sensors detected motion may emanate from the controller 118.

In some embodiments, a gait-pace meter 100 may comprise a second controller 124, and the second controller may operate similar to the controller 118 discussed above. A second controller 124 may also comprise a second display 126, and the second display 126 may be similar to the display 122 described above. Although a second controller 124 and/or second display 126 is not required for the systems described herein, in a bidirectional system, providing a controller 118,124 and/or a display 122,126 at both ends of a testing distance 110 may be helpful to a test administrator so the administrator is not required to walk to the opposite end of the testing site to view a calculated gait speed.

In some embodiments, once a sensor 106,108,114,116 detects motion, the sensors may cease sending signals to a controller 118,124. This means that, once the sensor is tripped (detects motion), additional movements in front of that sensor will not affect the quality of the data. This may be helpful for patients that need assistance walking. For example, a caretaker may walk behind the patient or beside the patient away from the sensors to aid in walking, and the sensors will not detect the caretaker's movements. In some embodiments, a controller 118,124 may censor values for gait speed that are not within the physiologic range of a human walking speed. For example and not limitation, if the system detects a gait speed of 2.5 m/sec, this may indicate that a sensor was accidentally triggered before a patient passed by the sensor. Accordingly, in some embodiments a controller 118,124 may censor the results by (1) not producing a gait speed result and/or (2) providing an error message that the test calculated an abnormal gait speed. In some embodiments, these censored ranges may be input into a display 122,126. A controller 118,124 may also receive input of an acceptable range of gait speeds.

In some embodiments, a gait-pace meter 100 may comprise a first initiation input 128. The first initiation input 128 may activate the system to begin a gait analysis. In some embodiments, the first initiation input 128 may be in communication with a controller 118,124 to activate a test; the communication being either a wired or a wireless communication. In some embodiments, providing input to a first initiation input 128 causes a first sensing unit 102 (or the sensors therein) to begin detecting motion. In some embodiments, providing input to a first initiation input 128 may also cause a second sensing unit 104 (or the sensors therein) to begin detecting motion. Providing an input to a first initiation input 128 may also cause a controller 118,124 to activate and become responsive to signals from the sensing units 102,104.

In some embodiments, a gait-pace meter 100 may comprise a second initiation input 130. A second initiation input 130 may be positioned at the opposite end of the gait-pace meter 100 from a first initiation input 128. The second initiation input 130 may operate in a manner similar to the first initiation input 128, but in the reverse direction. For example, in some embodiments, providing input to a second initiation input 130 causes a second sensing unit 104 (or the sensors therein) to begin detecting motion. The second initiation input 130 may also cause all sensing units 102,104 to begin detecting motion, similar to the first initiation input 128. Providing an input to a second initiation input 130 may also cause a controller 118,124 to activate and become responsive to signals from the sensing units 102,104.

In some embodiments, input to an initiation input 128,130 may cause only the closest sensing unit 102,104 to begin detecting motion. Using a first initiation input 128 as an example, a first initiation input 128 may receive input to begin a gait analysis. The connection between the controller 118,124 and the first sensing unit 102 may cause the first sensing unit's 102 sensors 106,114 to begin detecting motion. The sensors 108,116 in the second sensing unit 104 may not begin detecting motion until the first sensing unit 102 detects motions. Although this embodiment is not required for a gait-pace meter 100, it protects the distal (or farthest sensing unit away from the actuated initiation input) sensors from being inadvertently tripped if someone other than the patient passes a distal sensor before the patient reaches a proximal (or closest sensing unit) sensor. Also, the system may work bidirectionally, so the example above is also possible in the reverse direction.

An initiation input 128,130 may be any device allowing a test administrator to begin the gait speed analysis. In some embodiments, an initiation input 128,130 may be a button, including a mechanical button, a capacitive touch button, and/or or an inductive sensing button. In some embodiments, an initiation input 128,130 may be a touch-screen display. In some embodiments, an initiation input 128,130 may be a reader that only allows certain individuals to initiate a test. Examples of such readers include, but are not limited to, pads or screens for receiving passwords, RFID readers, magnetic-strip readers, biometric scanners, and/or any other secure reader or device. It is to be understood that, when this disclosure refers to an initiation input receiving an input, the input refers to any of these touches or inputs that may activate the system. In some embodiments, an initiation input 128,130 may be combined with a controller 118,124 and incorporated into a single device.

In some embodiments, an initiation input 128,130 may (1) provide instructions to a patient and (2) eliminate the errors associated with patient acceleration and/or deceleration. In some embodiments, when a test is initiated by an initiation input 128,130, the initiation input 130,128 at the opposite end of the testing distance 110 may provide a target to which the person being tested can walk. An initiation input 128,130 may be spaced apart from the opposite initiation input 130,128 at a distance greater than the testing distance 110. In some embodiments, an initiation input 128,130 may illuminate to become a target for the patient. As an example of this embodiment, a first initiation input 128 may receive an input to activate the gait-pace meter 100. This activation may cause the second initiation input 130 to illuminate, thus providing a target to which the patient can walk. The same can be performed in the reverse, wherein the second initiation input 130 receives an input and the first initiation input 128 illuminates to act as a target. In some embodiments, an initiation input 128,130 may provide an audible sound to which the patient can walk. By providing a target to which a patient can walk, many of the communication errors around gait speed analysis can be eliminated. For example, in any of the current methods of determining gait speed (e.g., stopwatch, pressure mat, RFID testing, etc.), a test administrator must make sure that the patient understands were the test begins and ends. The current systems and methods may provide additional feedback to ensure the patient walks across the entirety of the testing distance 110.

In some embodiments, the initiation inputs 128,130 may be positioned such that the patient does not accelerate or decelerate within the testing distance 110. If a patient accelerates after a starting point and/or decelerates before the end point of the test, the data will not represent a patient's customary gait speed. As described above, with current methods of determining gait speed, a test administrator must communicate, verbally, to a patient that they must continue walking past the start and finish line. It is to be expected that at least some amount of human error will exist when a patient (1) sees a start line and begins to accelerate to their customary gait and/or (2) sees a finish line and slowly decelerates as the patient approaches the line.

The present systems and methods are capable of lessening these human errors. In some embodiments, a gait-pace meter 100 may include an on-ramp (or acceleration zone 132) and an off-ramp (or deceleration zone 134). An acceleration zone 132 may be a distance between a beginning initiation input 128,130 and a beginning sensing unit 102,104; the deceleration zone 134 may be a distance between an ending sensing unit 102,104 and an ending initiation input 128,130. Using a first initiation input 128 and a first sensing unit 102 as an example, an acceleration zone 132 may be disposed between the first initiation input 128 and the first sensing unit 102. When a test administrator provides an input to the first initiation input 128, the patient can begin walking towards a finish line, which may be a second initiation input 130. The patient will be traveling at a customary gait speed when the patient passes the first sensing unit 102. The patient will continue past the second sensing unit 104 at a customary gait speed, and the patient will not begin decelerating until the patient is within the deceleration zone 134 disposed between the second sensing unit 104 and the second initiation input 130. Again, it is to be understood that any system described herein may be bidirectional, therefore the acceleration zone 132 can be disposed between the first initiation input 128 and the first sensing unit 102, and the acceleration zone 132 can be disposed between the second initiation input 130 and the second sensing unit 104. The same is true for the deceleration zone 134.

In some embodiments, an acceleration zone 132 and a declaration zone 134 may be of sufficient length to provide time to on-ramp to the testing distance 110 and off-ramp from the testing distance 110. In some embodiments, the acceleration zone 132 and/or deceleration zone 134 may be from between 2 feet and 20 feet; in some embodiments, the acceleration zone 132 and/or deceleration zone 134 may be equal to or greater than 3 feet. In some embodiments, the system does not include an acceleration zone 132 or a deceleration zone 134, but instead the patient begins and ends the test at the sensing units 102,104.

Figure 2:
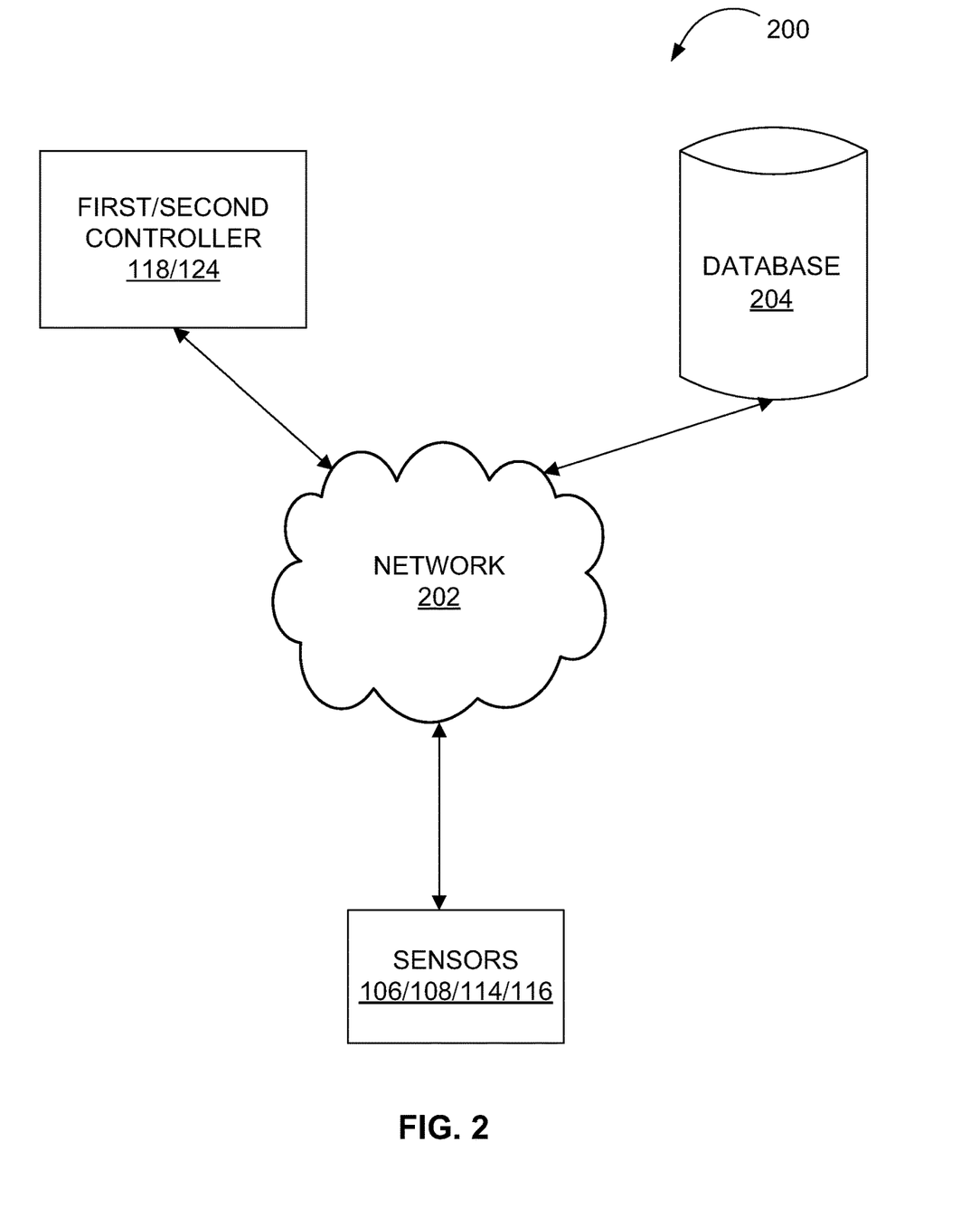
FIG. 2 is a diagram of an exemplary communication system that may transmit gait speed data to various internal and external components, according to some embodiments of the present disclosure.

FIG. 2 is a diagram of an example communication system 200 that may transmit gait speed data to various internal and external components, in accordance with some embodiments. As described herein, components of a gait-pace meter 100 may communicate with other components over a wired or wireless connection. In some embodiments, a sensor 106,108,114,116 may transmit a signal that the sensor detected motion to a controller 118,124 over a network 202. As described herein, a controller 118,124 may be a device dedicated to the gait-pace meter 100, but in other embodiments a controller 118,124 may be a separate computing device. A computing device may include a desktop computer or a mobile device, including a laptop computer, cellular phone, tablet, personal digital assistant, and/or any other computing device capable of receiving signals from a sensor 106,108,114,116, calculating a gait speed, and/or displaying a gait speed.

In some embodiments, the components of the system may also be in communication with a database 204. For example, a sensor 106,108,114,116 and/or a controller 118,124 may send data over a network 202 to a database 204. In some embodiments, a database 204 may store gait speed information for patients. A database 204 may store the gait speed information within a patient's healthcare file. In some embodiments, a database 204 may store information about a person's progression or regression over a period of time. For example, in some embodiments, the gait speed may be calculated daily, weekly, and/or monthly, and the information can be transmitted to the database 204. This would allow a patient or a physician to retrieve the information, via a device also connected to the network 202, and observe any trends in the patient's ambulation.

In some embodiments, the network 202 may be a wired connection between any of the components. In some embodiments, the network 202 may include individual connections via the internet, such as cellular or WiFi™ networks. In some embodiments, the network 202 may connect the sensors 106,108,114,116, controllers 118,124, and/or database 204 using other wireless connections, such as near-field communication (NFC), Bluetooth™, Bluetooth™ low-energy (BLE), ZigBee™, and/or ambient backscatter communications (ABC) protocols. If desired to keep certain information secret, such as for Health Insurance Portability and Accountability Act (HIPAA) purposes, one or more of these types of connections can be encrypted or otherwise secured.

Figure 3:
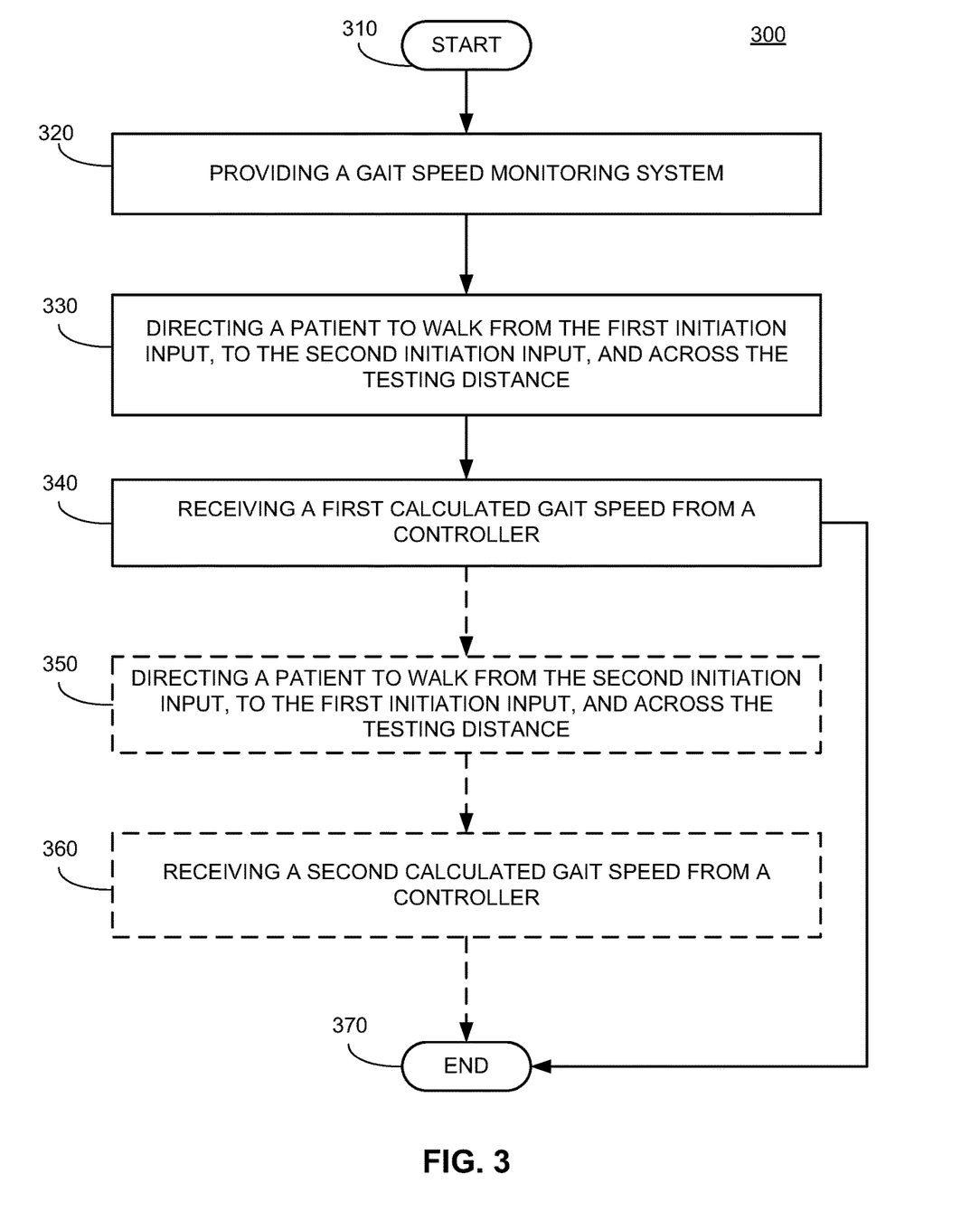
FIG. 3 is a process flow depicting an exemplary method of using a gait-pace meter, according to some embodiments of the present disclosure.

FIG. 3. is a process flow depicting an exemplary method 300 of using a gait-pace meter 100 as described herein, in accordance with some embodiments. The method 300 may begin 310 by providing a gait speed monitoring system 320. The gait speed monitoring may include any of the features described herein, including motion sensing units, one or more sensors for detecting motion (or presence), one or more controllers, one or more displays, and/or one or more initiation inputs. The administrator of the test may then direct a patient to walk from the first initiation input, to the second initiation input, and across the testing distance 330. As described herein, this step may also include activating the system by providing an input to an initiation input. If the gait-speed meter has an initiation input at both ends, the administrator can direct the patient to walk across the testing site by telling the patient to walk to the most distant initiation input. Again, the initiation inputs may include audible or visual feedback so that the initiation inputs become targets to which the patients can walk.

Once the patient has walked across the testing distance, the administrator can receive the gait speed from a controller 340. At this point, the test may conclude 370. However, as described herein, the systems and methods provide bidirectional testing. An administrator can, therefore, direct the patient to walk from the second initiation input, to the first initiation input, and across the testing distance 350 (i.e., in the reverse direction). Once the patient has walked across the testing distance, the administrator can receive a gait speed from a controller 360. In some embodiments, a controller may average a first calculated gait speed and a second calculated gait speed. The test may be concluded 370 after receiving a calculated gait speed. As described herein, receiving the gait speed may not be instantaneous, but rather the gait speed may be received at a database or at a separate computing device, depending on the needs of the clinical, hospital, or home use.

EXPERIMENTAL SECTION

The following section discusses tests performed on an embodiment of the presently disclosed systems. The trials were conducted on a system having two sensing units. Each sensing unit housed two sensors, one proximity sensor and one passive infrared motion detector. Each sensing unit also comprised a series of colored lights indicating the status of the sensors within the sensing units (red indicated an idle unit, green indicated an active unit, and blue indicated at least one of the sensors detected motions). The system comprised a controller at each end of the course. The controllers were wired to the sensing units so the controllers could receive the signals from the sensors. The controllers also provided audible feedback when sensors detected motion. The controllers also included a touchscreen display, which calibrated the testing distance and displayed the calculated gait speed.

The system comprised two initiation inputs, one below each controller. The initiation inputs were mechanical buttons that illuminated blue when the system was active, thus acting as a target to which the subject could walk. The system allowed the administrator to stand close to the patient while instruction were given, and the patient could walk to the opposite initiation input (target). The system comprised a 1-meter acceleration zone and a 1-meter deceleration zone. The testing distance was 4 meters. The system was bidirectional, as described herein.

A total of 10 participants, all healthy adults aged 65+, took part in the trials, and the 10 participants performed a total of 82 walks. The results for the system were compared against a pressure sensing mat by Protokinetics™ and against a stopwatch technique, the stopwatch being on a mobile phone application.

Figure 4:
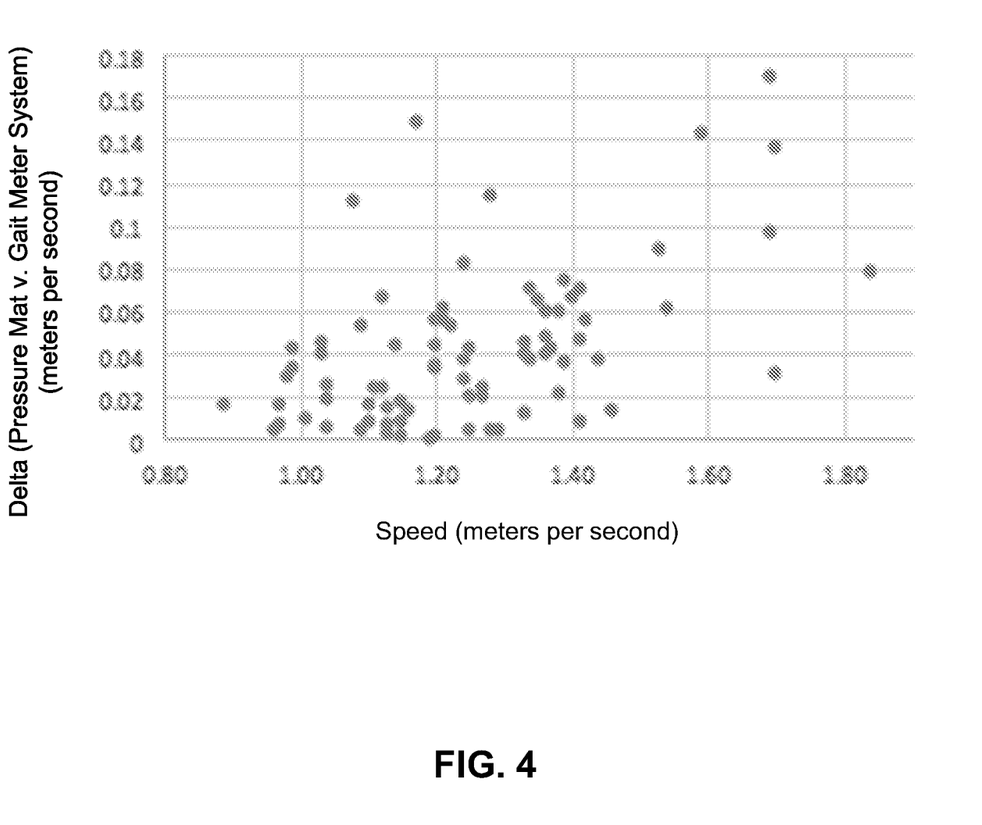
FIG. 4 presents results of a trial performed on a gait-pace meter and a pressure-sensing mat, and shows the differences in gait speed between the two systems, according to some embodiments of the present disclosure.

The gait meter system calculated gait speeds similar to that of the stopwatch and the pressure mat. The system registered an average difference of 0.03 m/s slower across the trials. One potential cause of this slower speed may be that the systems described herein track trunk speed and not footfall. The pressure mat inherently measure footfall, and the stopwatch method depends upon the test administrator's estimate of when the patient crosses the end line. The differences between the gait meter system and the two controls were greater at higher gait speeds. FIG. 4 shows this greater difference at higher speeds, as the figure provides the results of the gait meter system as compared to a pressure mat.

In summary, the present systems and methods offer a great amount of accuracy as compared to the gold standards. Additionally, the systems described herein offer an inexpensive and easy-to-use alternative to current systems. These systems, therefore, may provide the tools needed to make gait-speed analysis more common in primary-care settings.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A gait speed monitoring system comprising:
   a first motion sensing unit;
   a second motion sensing unit and spaced apart from the first sensing unit by a testing distance;
   a first initiation input configured to cause the first motion sensing unit to begin detecting motion;
   a second initiation input configured to cause the second motion sensing unit to begin detecting motion; and
   a controller configured to:
      receive a first signal from the first motion sensing unit when the first motion sensing unit detects motion;
      receive a second signal from the second motion sensing unit when the second motion sensing unit detects motion; and
      calculate a gait speed-based at least in part on:
         the first signal;
         the second signal; and
         the testing distance.

2. The system of claim 1, wherein the first motion sensing unit and the second sensing unit are positioned at a location selected from the group consisting of horizontal and in a walkway, from between 3 feet and 5 feet above a ground level of a walkway, upon a wall along a walkway, on a ceiling, and combinations thereof.

3. The system of claim 1, wherein the first initiation input is spaced apart from the second initiation input by an initiation distance greater than the testing distance.

4. The system of claim 1, wherein the first initiation input is spaced apart from the first motion sensing unit by a distance of at least 3 feet; and
wherein the second initiation input is spaced apart from the second motion sensing unit by a distance of at least 3 feet.

5. The system of claim 1, wherein one or both of the first initiation input and the second initiation input is configured to illuminate as a walking target.

6. The system of claim 1, wherein one or both of the first initiation input and the second initiation input is configured to provide an audible signal as a walking target.

7. The system of claim 1, wherein the controller is further configured to one or both:
upon an input to the first initiation input, cause the second initiation input to illuminate as a walking target; and
upon an input to the second initiation input, cause the first initiation input to illuminate as a walking target.

8. A gait speed monitoring system comprising:
a first sensing unit comprising a first sensor;
a first initiation input configured to activate the first sensing unit;
a second sensing unit comprising a second sensor, and spaced apart from the first sensing unit by a testing distance;
a second initiation input configured to activate the second sensing unit and spaced apart from the first initiation input by an initiation distance; and
a controller configured to:
initiate the first initiation input to activate the first sensing unit, and begin detecting motion;
receive a first signal from the first sensor representative of the first sensor detecting motion;
initiate the second initiation input to activate the second sensing unit, and begin detecting motion;
receive a second signal from the second sensor representative of the second sensor detecting motion; and
calculate a gait speed based at least in part on:
the first signal;
the second signal; and
the testing distance;
wherein the first sensing unit is configured to provide at least one of a visual or audible feedback when the first sensor detects motion; and
wherein the second sensing unit is configured to provide at least one of a visual or audible feedback when the second sensor detects motion.

9. The system of 8, wherein the first sensor is one of a passive infrared motion detector, a proximity sensor, or an ultrasonic rangefinder; and wherein the second sensor is one of a passive infrared motion detector, a proximity sensor, or an ultrasonic rangefinder.

10. The system of 8, wherein the controller is a mobile device.

11. The system of 8 further comprising a display unit configured to display the gait speed.

12. The system of claim 11, wherein the display unit is a mobile device.

13. The system of 8, wherein the controller is further configured to transmit the gait speed to a database.

14. The system of 8, wherein the controller is further configured to:
compare the calculated gait speed to a predetermined range of acceptable gait speeds; and
censor the calculated gait speed if the calculated gait speed is outside of the predetermined range of acceptable gait speeds.

15. A method of calculating gait speed comprising:
initiate a first initiation input to activate a first sensing unit comprising a first sensor to begin detecting motion;
initiate a second initiation input to activate a second sensing unit comprising a second sensor to begin detecting motion;
wherein the first sensing unit is spaced apart from the second sensing unit by a testing distance; and
wherein the first initiation input is spaced apart from the second initiation input by an initiation distance;
direct a patient to traverse at least the testing distance;
receive a first signal from the first sensor representative of the first sensor detecting motion of the patient;
receive a second signal from the second sensor representative of the second sensor detecting patient; and
calculate a gait speed of the patient based at least in part on:
the first signal;
the second signal; and
the testing distance.

16. The method of claim 15, wherein the initiation distance is greater than the testing distance.

17. The method of claim 16, wherein the first initiation input is spaced apart from the first sensing unit by a distance of at least 3 feet; and
wherein the second initiation input is spaced apart from the second sensing unit by a distance of at least 3 feet.

18. The method of claim 16, wherein one or both of the first initiation input and the second initiation input is configured to illuminate as a walking target.

19. The method of claim 16, wherein one or both of the first initiation input and the second initiation input is configured to provide an audible signal as a walking target.

20. The method of claim 15, wherein the first sensing unit is configured to provide at least one of a visual or audible feedback when the first sensor detects motion; and
wherein the second sensing unit is configured to provide at least one of a visual or audible feedback when the second sensor detects motion.

* * * * *